(12) United States Patent
Pettersson (10) Patent No.: US 6,478,747 B1
(45) Date of Patent: Nov. 12, 2002

(54) METHOD AND DEVICE TO SENSE BREATHING

(75) Inventor: Hans Pettersson, Linghem (SE)

(73) Assignee: Optovent Aktiebolag (publ), Bromma (SE)

( * ) Notice: Subject to any disclaimer, the term of this patent is extended or adjusted under 35 U.S.C. 154(b) by 0 days.

(21) Appl. No.: 09/462,906

(22) PCT Filed: Jul. 20, 1998

(86) PCT No.: PCT/SE98/01404

§ 371 (c)(1),
(2), (4) Date: Mar. 15, 2000

(87) PCT Pub. No.: WO99/03395

PCT Pub. Date: Jan. 28, 1999

(30) Foreign Application Priority Data

Jul. 18, 1997 (SE) .............................................. 9702756

(51) Int. Cl.[7] .................................................. A61B 5/00
(52) U.S. Cl. ...................................................... 600/538
(58) Field of Search ....................... 128/200.28, 204.23, 128/206.28–206.29; 600/529, 532, 538

(56) References Cited

U.S. PATENT DOCUMENTS

| | | | | |
|---|---|---|---|---|
| 5,074,299 A | * | 12/1991 | Dietz | 128/204.21 |
| 5,676,154 A | * | 10/1997 | Pettersson | 600/538 |
| 5,782,240 A | * | 7/1998 | Raviv et al. | 600/529 |
| 6,045,514 A | * | 4/2000 | Raviv et al. | 600/529 |

FOREIGN PATENT DOCUMENTS

WO  96/41571  * 12/1996 ................. 600/534

* cited by examiner

*Primary Examiner*—Robert L. Nasser
(74) *Attorney, Agent, or Firm*—Young & Thompson

(57) ABSTRACT

Method and devices intended to be used at sensing of breathing of a man or an animal in order to with a breathing sensor securely sense the breathing regardless of whether it occurs through the nose or mouth. A device (1) conducts breathing air flows to and from the nose as well as the mouth past a position (5), at which the sensor is located. In one embodiment the device is tubular and has two orifices (2, 3) for location at the nose and mouth respectively, as well as a third orifice (5) onto which a sensor may be fastened by snap action.

8 Claims, 7 Drawing Sheets

METHOD AND DEVICE TO SENSE BREATHING

CROSS REFERENCE TO RELATED APPLICATION

This is the national stage application of international application PCT/SE98/01404 filed on Jul. 20, 1998, which designated the United States of America.

FIELD OF THE INVENTION

The present invention refers to a method and assisting devices intended to be used to sense the breathing of a man or an animal.

With "to sense breathing" in this document is referred primarily to achieve a signal which to a substantial extent follows the breathing air flow.

BACKGROUND OF THE INVENTION

In connection to utilization of an equipment to sense breathing according to the international patent application WO 94/16620 a breathing sensor should be placed so that it is located in the breathing air flow at exhaling as well as inhaling. This is exemplified in the application by a retainer that is applied in a nostril.

SUMMARY OF THE INVENTION

A problem that is solved by the present invention, is by means of a breathing sensor to reliably sense the breathing regardless of whether it occurs through the nose or mouth. Another problem that is solved is to securely hold the breathing sensor in its position and simply be able to apply and remove the same. Moreover it should be possible to move the sensor from one patient to another without a risk of transmisson of infection. A further problem that is solved is to give small influence on normal breathing. These and other problems are solved by a method and devices according to the following patent claims.

In the first place thus a device is used that conducts breathing air flows to and from the nose as well as the mouth past a position at which the sensor is placed so that breathing detection may take place irrespective of how breathing occurs.

In a first embodiment a tubular device is used that is fixed between and with an end orifice at each of the nose and mouth and a third orifice of the sensor placed on the tubular device. This embodiment includes three main parts: the tubular device, a fastening plate for the tubular device and a sensor retainer which can be fastened to the device by snap action. A second embodiment is constituted mainly by a convexly rounded part intended to be fastened above the nose and mouth together with the first embodiment and formed such that it captures the breathing air flows and leads them to the orifice of the sensor. The tubular as well as the convexly rounded part are designed such that they do not constitute any obstruction for normal breathing. A variant of the convexly rounded part is provided to be able to be used together with a nasal canula. The sensor retainer according to the invention can also be used for patients that have been intubated, whereby a special intermediate part with a connection tube piece for the sensor retainer is used.

In a third embodiment, the tubular device is externally shaped with a flattened portion which is provided with adhesive means so that a special fixing plate is not required to fasten the tubular device to the upper lip. This embodiment can also be designed to be directly fastened to a nasal canula without requirement of the convexly rounded part according to the second embodiment.

The devices according to the invention not only may be used with an equipment of the type mentioned above that utilizes a fibre end in the breathing air flow, but also together with other breathing sensors intended to be placed in breathing air flow, for example such being based on temperature sensing.

Devices that utilize hoses to conduct air flows from nose and mouth respectively to a common breathing sensor are known through WO 9641571 A (FIG. 8a, claims 1–10) and WO 9705824 A1 (FIG. 5). Moreover, devices with several sensors for sensing mouth and nose breathing are known through the above references, as well as U.S. Pat. No. 5,069,222 A and U.S. Pat. No. 5,413,111 A.

BRIEF DESCRIPTION OF THE DRAWINGS

The invention will now be described in greater detail in connection to the drawing.

FIGS. 1A, 1B and 1C shows a tubular device according to a first embodiment of the invention in which

FIG. 2 in three views shows a retainer of a device according to FIG. 1, where

FIG. 3 shows in three partial figures a second embodiment of a retainer similar to that of FIG. 2. FIG. 3A thus shows a frontal view, FIG. 3B a view from below while

FIG. 4 in three views and two sections shows a fibre retainer intended to be releasably fastened to the device according to FIG. 1. FIGS. 4A, 4D and 4E thus shows three partial views, while

FIG. 5 in three partial views.

FIG. 6 in two views, from the front according to FIG. 6A and laterally according to FIG. 6B, shows a second embodiment of the convexly rounded part according to FIG. 5, intended to be used with a nasal camula.

FIG. 7 shows an intermediate piece with a connection pipe intended to be used at intubation. FIG. 7A shows the intermediate piece from one side and FIG. 7B shows a section A—A according to. FIG. 7A.

FIGS. 8A, 8B and 8C shows a third embodiment of the invention corresponding to the tubular device 1 in FIGS. 1A, 1B and 1C, where

DESCRIPTION OF THE PREFERRED EMBODIMENTS

Figure 1A:
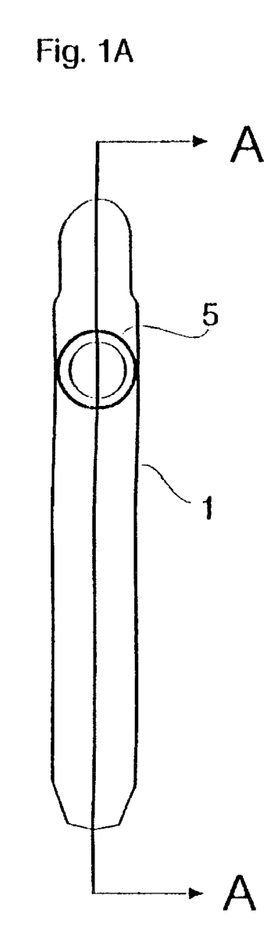
FIG. 1A shows a frontal view.
Figure 1B:
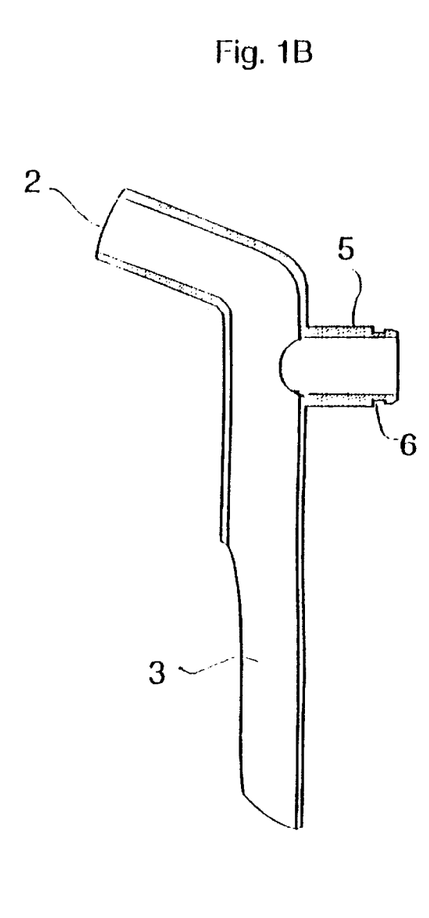
FIG. 1B shows a section A—A according to FIG. 1A.
Figure 1C:
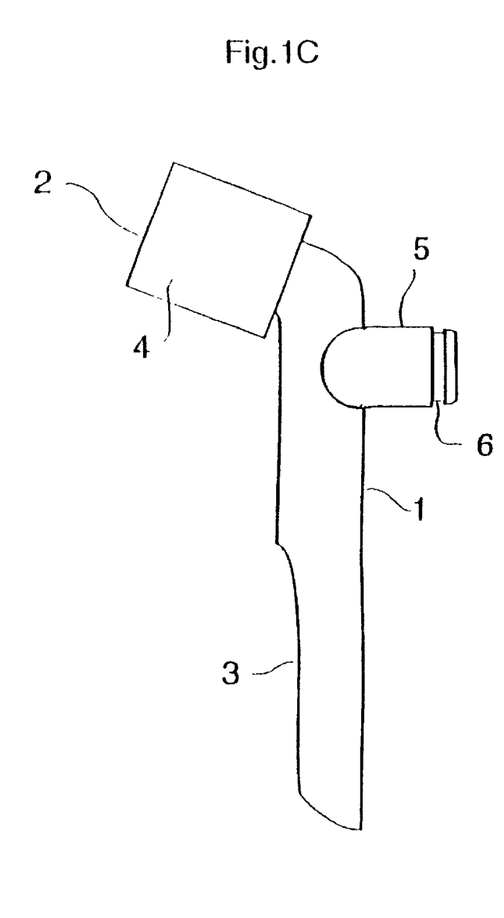
FIG. 1C shows a lateral view with a nose ring mounted.

The embodiment of the invention according to FIGS. 1A–C consists of a tubular part 1 with a first end orifice 2 and a second end orifice 3 and a channel interconnecting the orifices. At the first end orifice 2 the tube is cut mainly perpendicularly. In proximity to the first end orifice 2 the tubular part 1 is angled about 70 degrees so that the first end orifice can be directed inwards towards air channels in the nose when it is placed in a nostril. A sealing ring 4 of slow elastic foam plastic is arranged on the tubular part 1 at the first end orifice 2 (FIG. 1C). The other end orifice 3 of the tubular part 1 is also open a portion along the longitudinal direction of the tubular portion and it is this opening that is intended to be placed over the mouth when the device is used.

A tube piece 5 which is connected to the inner channel of the tubular part 1 is located on the tubular part so that there is formed almost a straight line for an airflow from the first end orifice 2 to the tube connector 5, which thus exhibits a third end orifice. This dimensioning has proven to give good breathing detection at nasal as well as oral breathing. The pipe connector 5 at its end is provided with a groove 6 in order to faciliate fastening of a sensor part by snap action.

A retainer in the shape of a plate 7 with a tube part 10 (FIG. 2) is intended to keep the tubular part 1 in place by threading this through the tube part 10 and the plate 7 is adhered to the upper lip. The plate 7 is also provided with holes 8,9 so that the device if necessary can be fixed by means of a rubber string or the like round the head. In addition the plate 7 is provided with an adhering layer 11.

Figure 3A:
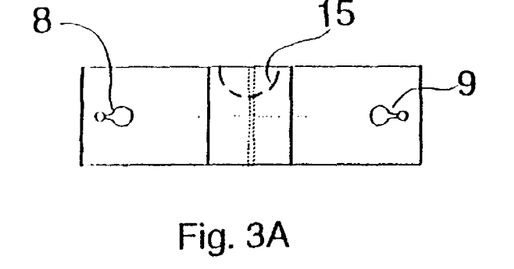
Figure 3B:
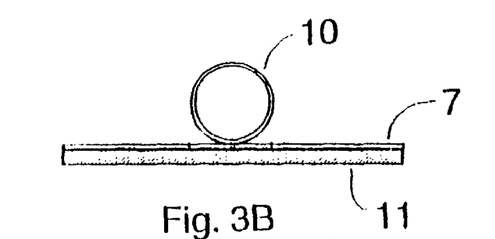
Figure 3C:
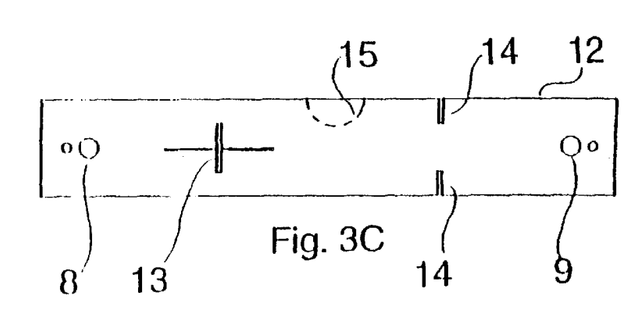
FIG. 3C shows how the retainer can be made from a material strip.
Figure 4A:
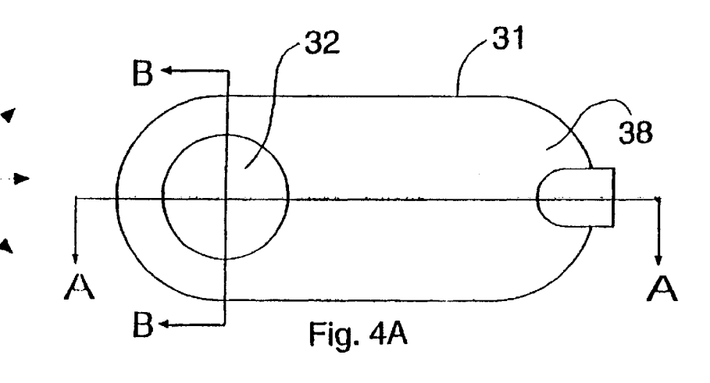
Figures 4B, 4C:
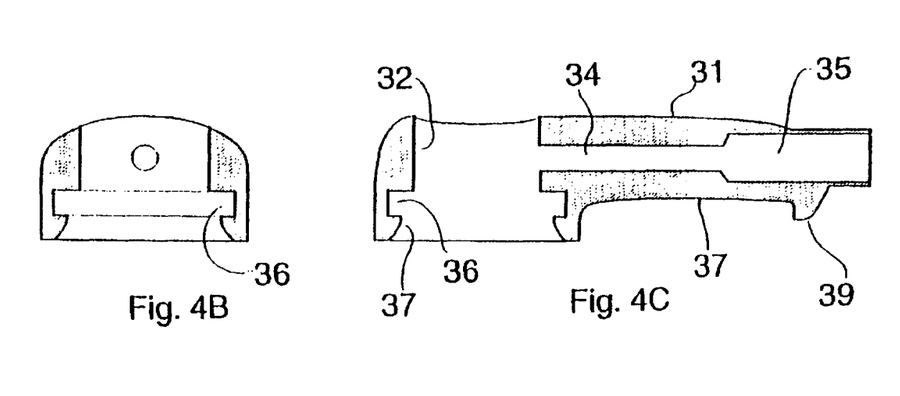
FIG. 4B and FIG. 4C show sections according to B—B and A—A in FIG. 4A respectively.
Figure 4D:
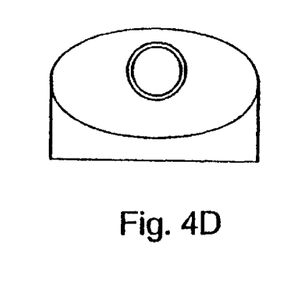
Figure 4E:
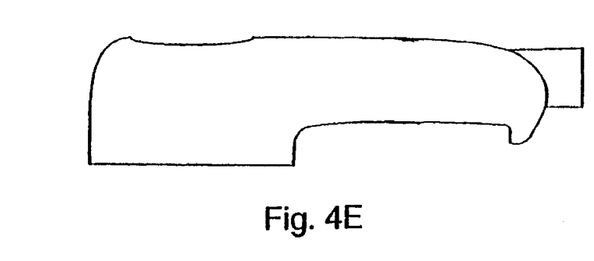

In an alternative embodiment of the retainer according to FIGS. 3 (3A, 3B, 3C) this consists of a strip 12 according to FIG. 3C. The strip 12 is provided with a cross shaped groove 13 and two opposite grooves 14 so that one of the ends of the strip 12 may be threaded through the cross shaped groove 13 until the opposite grooves 14 come into engagement with the groove 13 and tube part 10 and the plate 7 is formed by the strip 12.

Figure 2A:
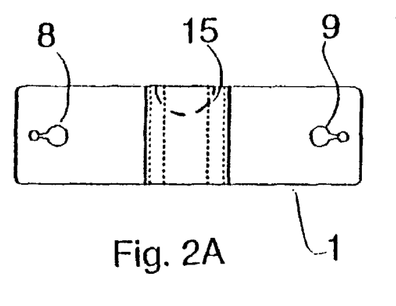
FIG. 2A shows a frontal view.
Figure 2B:
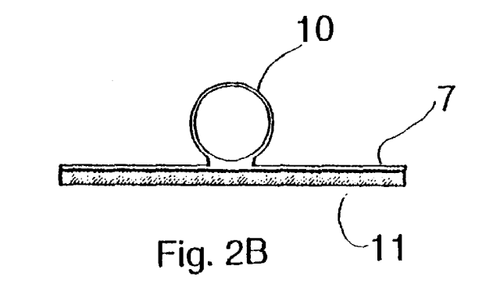
FIG. 2B shows a view from below and FIG. 2C shows a lateral view.
Figure 2C:
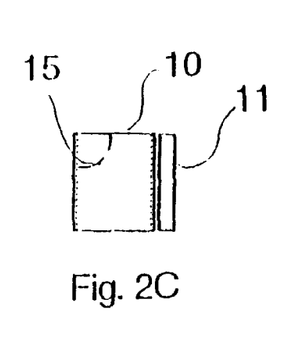

As indicated in FIGS. 2 and 3 the retainers may be provided with recesses 15 on the tubular part 10, whereby the recesses 15 are adapted to receive the tube connector 5 thereon. As an alternative to the retainers according to FIGS. 2 and 3 the tubular part 1 may be provided with a fastening plate.

The fibre retainer according to FIG. 4 is intended to protect the end of an optical fibre which constitutes the breathing sensor, and faciliate its location on the assisting devices according to invention. The fibre retainer 30 is. shown in three projections in FIGS. 4A, 4D and 4E and in two sectional views according to B—B in FIG. 4B and A—A in FIG. 4C respectively. It consists of a longish part 31 which at one end has a substantially cylindric air duct 32 passing through. A channel 34 runs through the longish part 31 and mainly perpendicularly versus the air duct 32 adapted for an optical fibre (not shown), which in a mounted state is retained in the fibre retainer so that the fibre end is located centrally in the air duct 32. The fibre channel 34 is provided with an expanded portion 35 with a diameter corresponding to the protection cover of the fibre. One end of the air duct 32 is funnel-shaped widened and provided with a groove 36 so that a flange 37 is formed. The flange 37 is adapted to be received in the groove 6 so that the fibre retainer can be snapped onto the connecting tube 5. The longish portion of the fibre retainer 31 is flattened and is provided with opposite grip surfaces 37 and 38 as well as a protrusion 39 in order to faciliate its fastening and removal. In those cases where the invention is used together with sensors other than optical fibers only the fibre retainer needs to be modified and adapted to the sensor type in question.

Figure 5A:
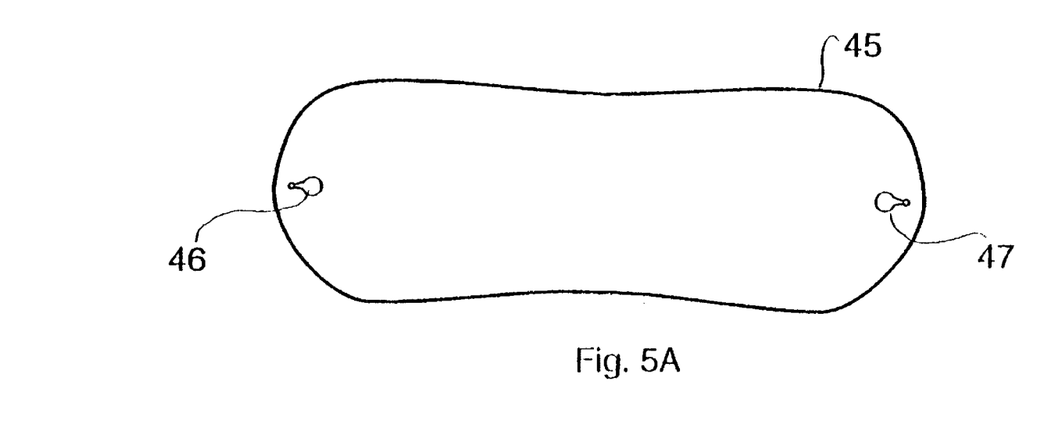
FIGS. 5A, 5B and 5C shows a second embodiment in the form of a convexly rounded part which can be used with the devices according to FIGS. 1–4.
Figure 5B:
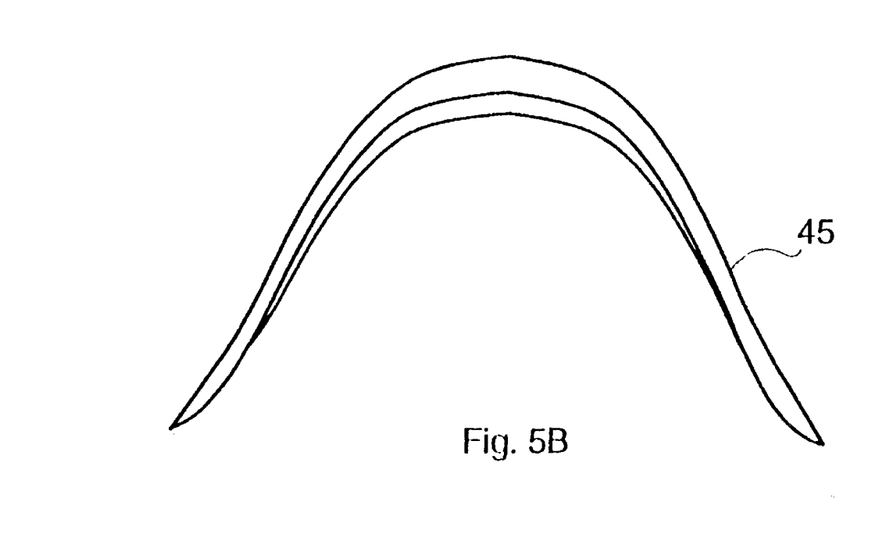
Figure 5C:
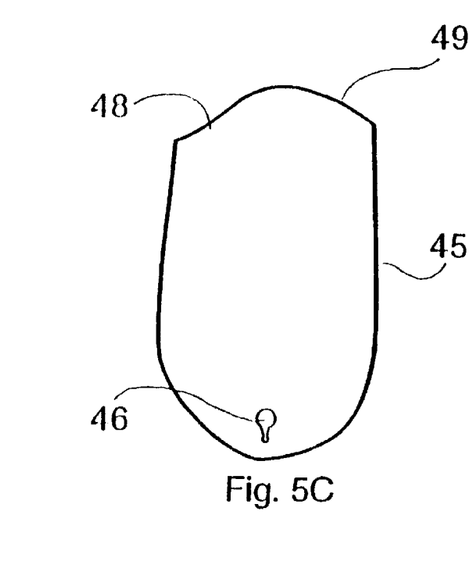

The device according to FIGS. 5A, 5B and 5C is constituted by a convexly rounded part 45 of a thin material of substantially uniform thickness, intended to be placed above parts of nose and mouth of a patient and is used together with devices according to FIGS. 1–4. The convexly rounded part 45 is provided with holes 46, 47 so that it can be fastened around the head by means of a rubber string or the like. It has a dome-shaped, somewhat unsymmetrical form with a convex portion 49 seen in section from outside and a somewhat concave portion 48. It is shaped such that its position can be tested out for the individual patient with either the convex or the concave portion directed upwards against the nose, in order to achieve the best possible respiratory detection by means of the device according to FIG. 1 by nasal breathing as well as oral breathing. The reason why a convexly rounded portion 45 sometimes is required is that certain patients especially by oral breathing have a weak and uneven breathing air flow.

Figure 6A:
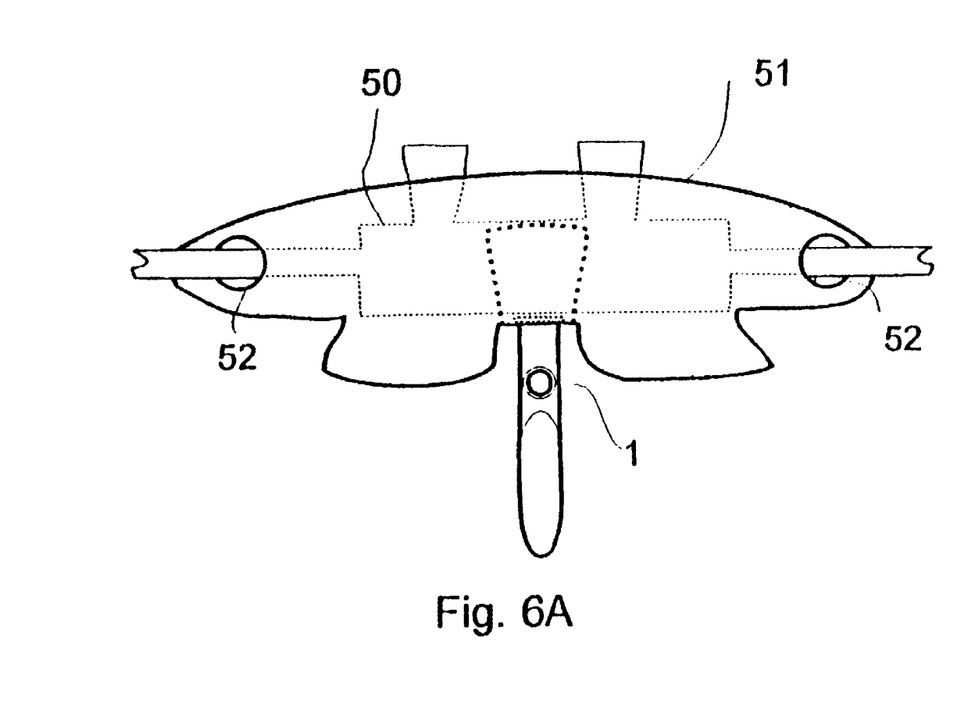
Figure 6B:
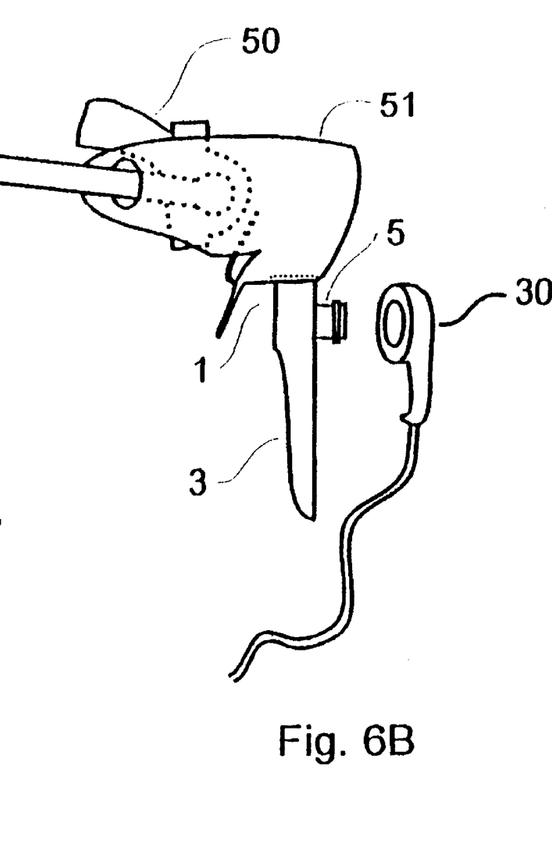

The device according to FIGS. 6A and 6B constitutes an alternative to the embodiment according to FIGS. 5 A–C. In the first place it is intended to be used with a nasal canula 50 which is used to supply oxygen to both nostrils. It mainly consists of a convexly rounded device 51 provided with two holes 52 so that it can be threaded over the nasal canula and held in place under the nose by this. Thus the convexly rounded device 51 can serve as a retainer for a tubular device 1 according to FIG. 1 or placed above a separately retained tubular device 1. The convexly rounded device 51 then captures the breathing flow at nasal breathing and leads it to the the upper orifice 2 while the lower orifice 3 normally is held in place in front of the mouth and captures the breathing air flow by oral breathing.

Figure 7A:
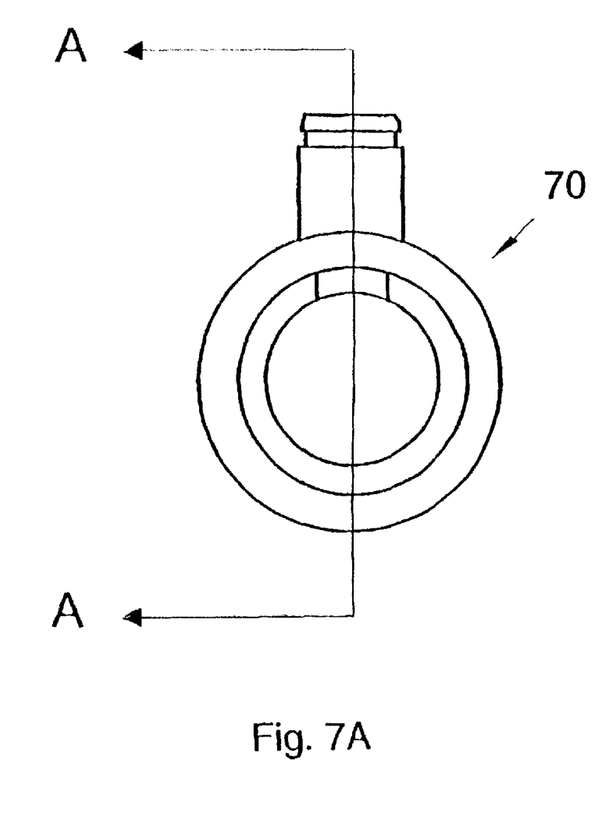
Figure 7B:
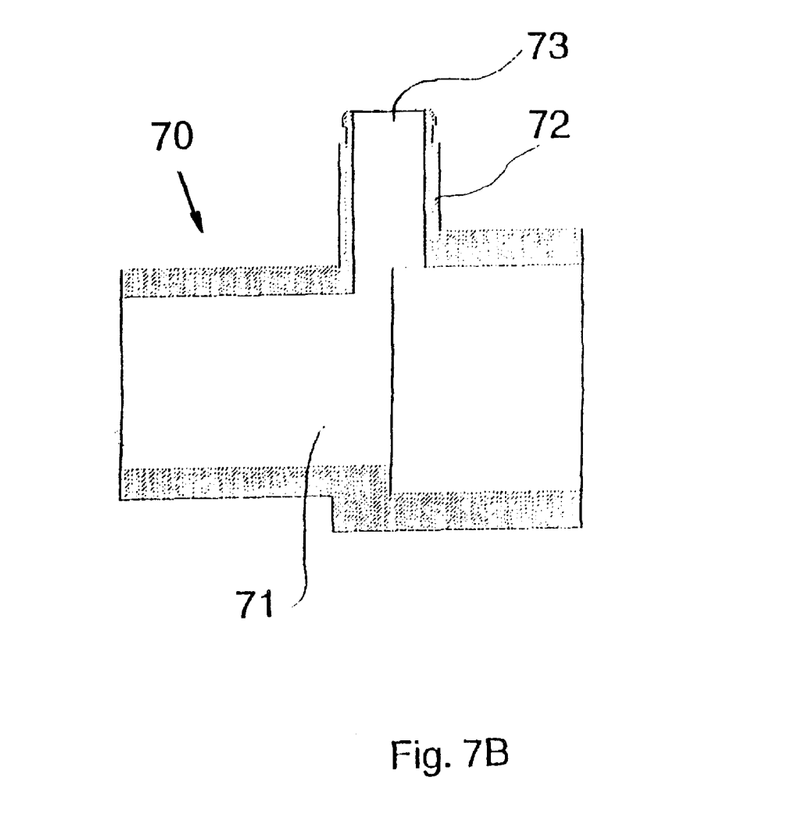

The intermediate piece 70 according to FIGS. 7A and 7B is provided with a through channel 71 which can be coupled to a tracheal tube and is provided with a connection tube 72 with a cross channel 73 similar to the tube connecting piece 5. By intubated patients the intermediate piece 70 can be used with the fibre retainer 30 instead of the tubular device 1, whereby a reliable detection of the breathing may be carried out.

Figures 8A, 8B, 8C, 9A, 9B, 9C, 9D:
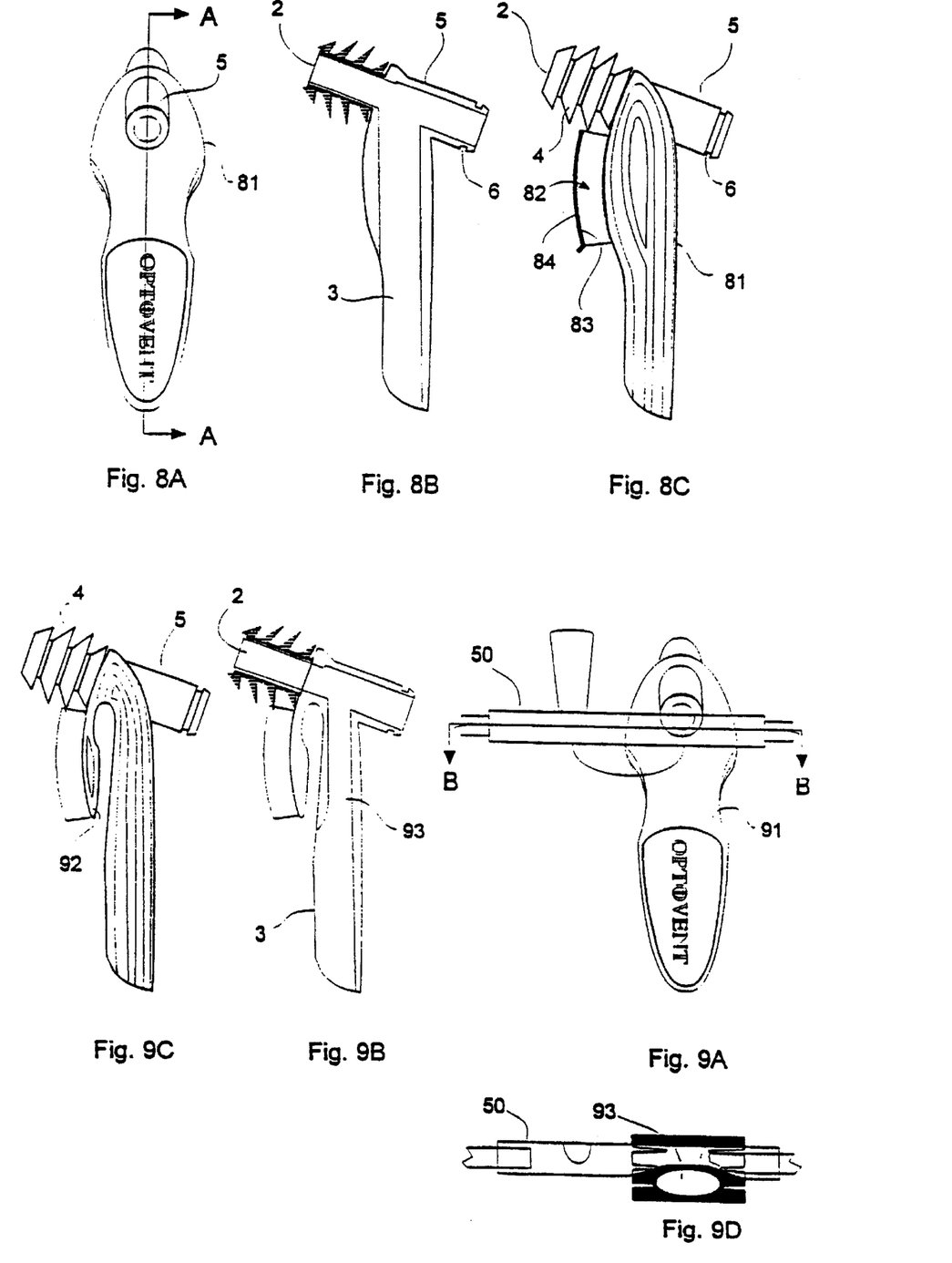
FIG. 8A shows a frontal view.
FIG. 8B shows section A—A according to FIG. 8A.
FIG. 8C shows a lateral view with a nose ring mounted.
FIGS. 9A, 9B, and 9C shows a modified version for a nasal canula of the device according to FIGS. 8A, 8B and 8C with corresponding partial views.
FIG. 9D shows a section B—B according to FIG. 9A.

In the embodiment according to FIGS. 8A, 8B and 8C the tubular device 1 shown in FIGS. 1A, 1B and 1C is replaced by an adapter device 81 which has an essentially similar inner channel between the first end orifice 2 and the second end orifice 3 as the tubular device 1, but externally has a longish flattened portion along the second end orifice 3 and the main portion of the inner channel. The longish flattened portion, which constitutes the main portion of the adapter device 81, is designed with a waist of grip surfaces in order to faciliate application, and above the other, longish end orifice 3 is provided with a dome-shaped portion, on which a cushion 82 of resilient material e.g. foam plastic has been applied, outwards provided with an adhesion means 83 with a covering protection film 84. Through this design the adapter device 81 can be fastened directly on the upper lip after tearing off the protection film 84 and no further retainer is required.

In the adapter device 81 the connection tube 5 is arranged in a straight line with the air flow from the first end orifice 2, while the channel from the second end orifice 3 forms an angle of about 70 degrees with the connection tube 5. The sealing ring 4 in this case is constituted by ring-shaped flanges of resilient material. The cross-sectional areas of the air channels from the end orifices 2 and 3 and in the connection tube 5 are adapted to give detectable breathing air flow through the connection tube 5 regardless if nasal or oral breathing occurs when the first end orifice 2 is located in or at a nostril and the second end orifice 3 outside the mouth of a measuring object.

FIGS. 9A, 9B, 9C and 9D shows how the device according to FIGS. 8A, 8B and 8C may be modified to be used in connection with a nasal canula 50. The main portion of the adapter device 91 has thus been formed with a tongue 92 which can be threaded over and hung on the nasal canula and replace one of its orifices, which has been removed. Oxygen via the nasal canula is then supplied via one of the nostrils while breathing measurement may be performed by the adapter device 91 in the other nostril. In order to allow an air flow large enough at oral breathing from the second end orifice 3 to reach the connection tube 5, the intermediate air channel 93 at the tongue 92 has been given an oblong cross section, see FIG. 9D. As in the adapter device 81 in this case the tongue 92 has been provided with a pad 82 with adhesion means 83 and a protection film 84.

Other designs are also possible within the scope of the following patent claims.

What is claimed is:

1. A method to sense breathing of a man or an animal, which comprises:

providing a device that conducts breathing air flows from a nose as well as a mouth, said device comprising a short tubular part having a first orifice at a first end, a second orifice at a second end, a channel between said first end and said second end, a third orifice positioned on the tubular part and communicating with the channel, and a pad having an adhering part for retaining the tubular part on a patient;

providing a single sensor that is influenced by a breathing air flow, and comprises an optical fiber; and applying said sensor on said third orifice, whereby breathing detection may be carried out by said sensor.

2. A device comprising a single sensor to sense breathing of a man or an animal by conducting a breathing air flow from a nose and a breathing air flow from a mouth to the single sensor which comprises an optical fiber that is influenced by breathing air flows, said device further comprising: a tubular part having a length substantially equal to a distance between the mouth and a nostril; said tubular part comprising a channel and a first part to conduct breathing air flow through said channel and adapted to be placed at the nose or in a nostril; a second part to conduct breathing air flow through said channel and adapted to be placed in or in front of the mouth; an end orifice connected to said channel between a first end and a second end of the tubular part, at which the sensor is adapted to be placed; and a pad having an adhering part for retaining the tubular part on a patient.

3. The device according to claim 2, wherein the first end of the tubular part is provided with a first orifice, and the second end of the tubular part is provided with a second orifice.

4. The device according to claim 2, further comprising a plate having an adhering layer for retaining the tubular part on a patient; said plate being provided with a tube part for accommodating the tubular part.

5. The device according to claim 2, wherein the end orifice of the sensor is provided with means for releasably holding a sensor unit which contains the breathing sensor.

6. The device according to claim 5, wherein the sensor unit includes an elongated part with a substantially cylindrical air duct passing therethrough, and an end of an essentially radially arranged optical fiber is located at the center of said air duct.

7. The device according to claim 6, wherein the air duct is arranged through the elongated part at one end thereof, while the other end is shaped as a handle part.

8. The device according to claim 2, wherein said device further includes a convexly rounded part adapted to be fastened over at least parts of the nose, mouth and the sensing device.

* * * * *